United States Patent [19]

Aviles, Jr.

[11] Patent Number: 4,662,352

[45] Date of Patent: May 5, 1987

[54] CATALYTIC HEATING SYSTEM

[75] Inventor: Ernesto R. Aviles, Jr., San Diego, Calif.

[73] Assignee: Applinc, Lancaster, Calif.

[21] Appl. No.: 586,125

[22] Filed: Mar. 5, 1984

[51] Int. Cl.$^4$ .......................... A61F 7/08; A62B 7/08
[52] U.S. Cl. .............................. 126/204; 128/204.17; 128/202.26; 422/122; 422/195; 422/197
[58] Field of Search ............... 431/268, 326; 128/204.17, 202.26, 212, 186, 192, 142.4, 146.3; 126/204; 422/122, 187, 193, 195, 197, 238

[56] References Cited

U.S. PATENT DOCUMENTS

| | | | |
|---|---|---|---|
| 3,385,286 | 5/1968 | Jones | 126/204 |
| 3,898,049 | 8/1975 | Burroughs et al. | 422/195 X |
| 4,008,050 | 2/1977 | Betz | 422/195 X |
| 4,016,878 | 4/1977 | Castel et al. | 126/204 X |

Primary Examiner—Randall L. Green
Attorney, Agent, or Firm—James W. McClain; Stanley A. Becker

[57] ABSTRACT

An improved catalytic heater for heating an oxidizing gas, normally air, that contains a small percentage of a catalytically oxidizable gas, normally hydrogen, and a novel method of operation within the catalytic heater. A preheat catalytic chamber is defined within a primary catalytic chamber, and the air/hydrogen mixture is first flowed through the preheat chamber and then through the primary chamber, so that the gas will first be catalytically preheated as it passes through the preheat chamber and will be further heated within increased thermodynamic efficiency because of the preheating as it passes through the primary chamber. The preheat chamber is defined within massive heat sink means, preferably of brass, which obtains additional heat from the primary catalytic chamber so as to cause the preheat catalytic activity to be even further effective for overall increased thermodynamic effiency of the system, and the heat sink characteristic stabilizes the output temperature of the heated gas against fluctuations such as may be caused when the gas is employed as a breathing gas. A principal use of the invention is for breathing to overcome hypothermia.

3 Claims, 8 Drawing Figures

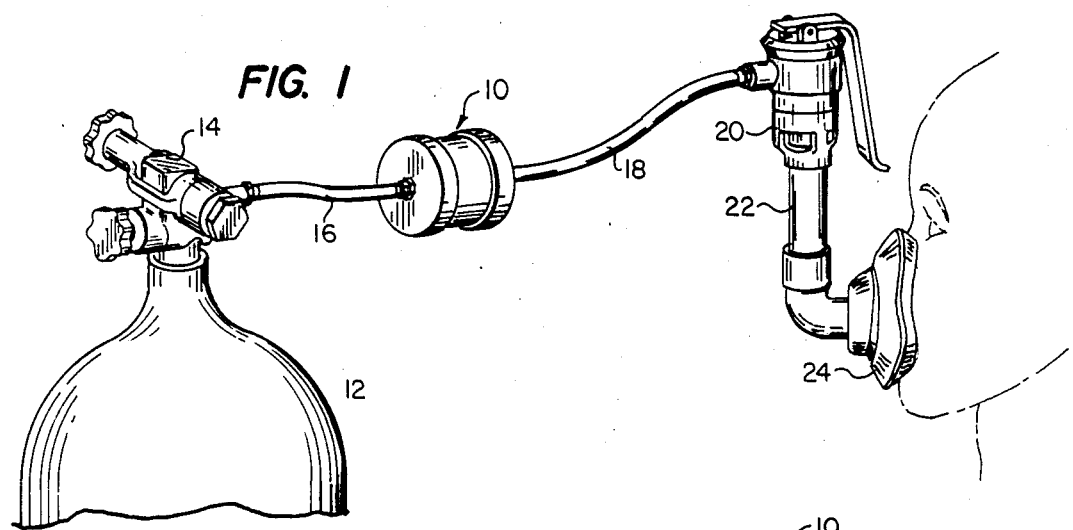
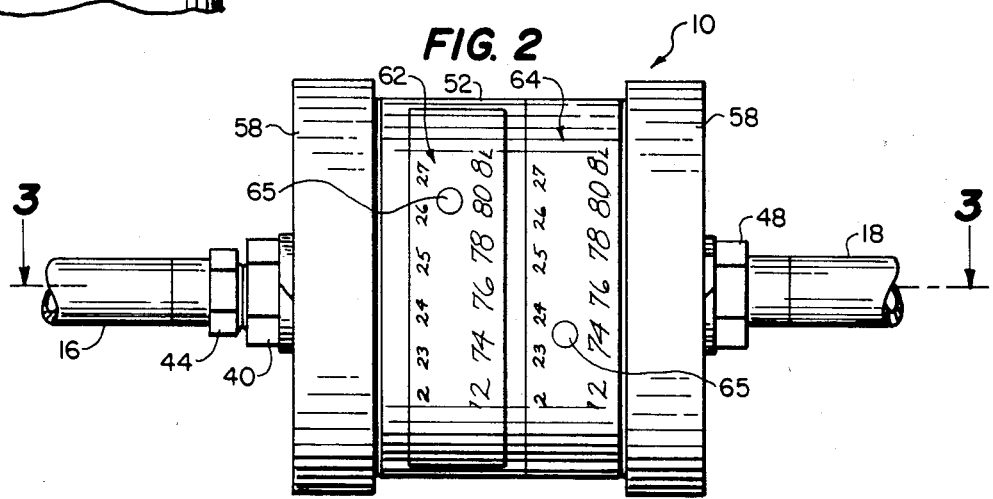
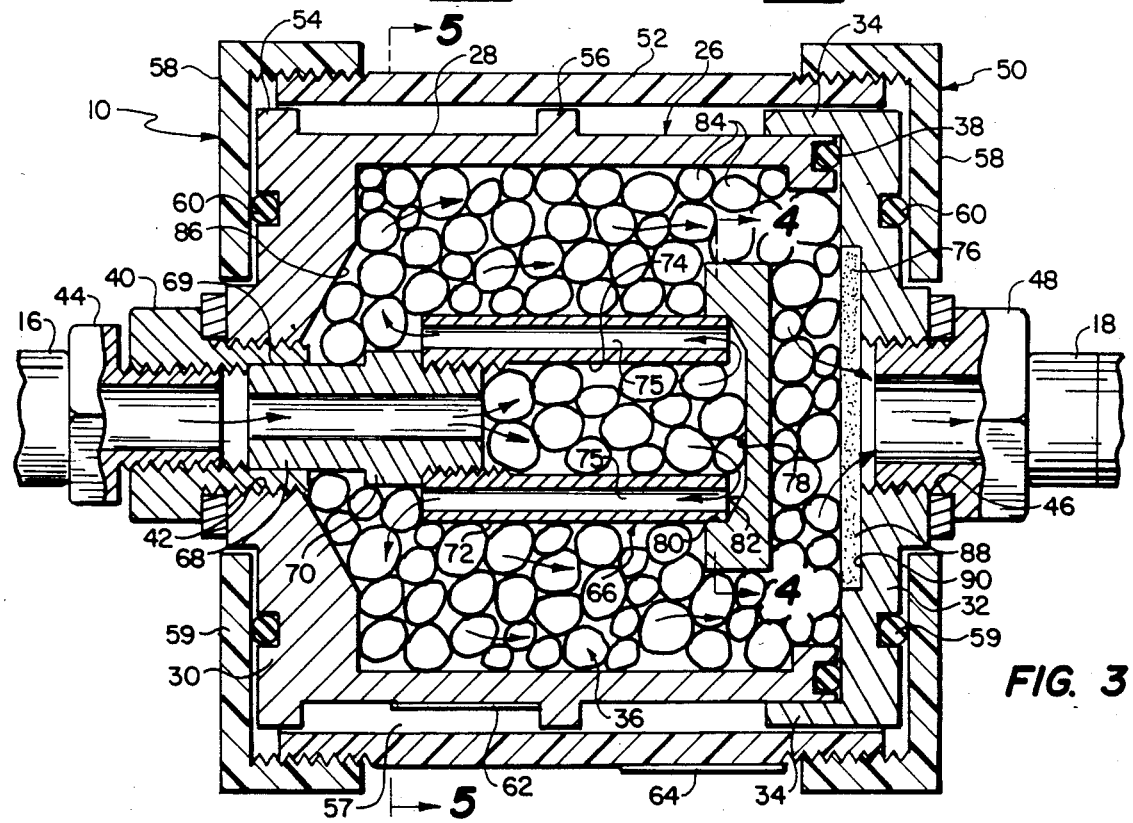

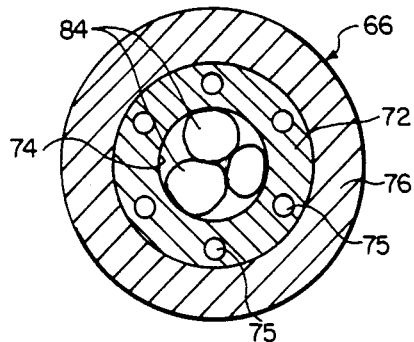
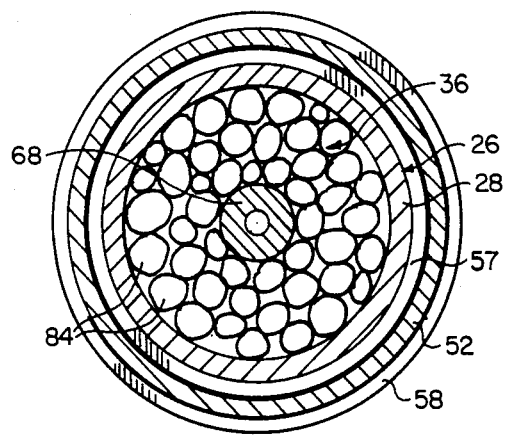
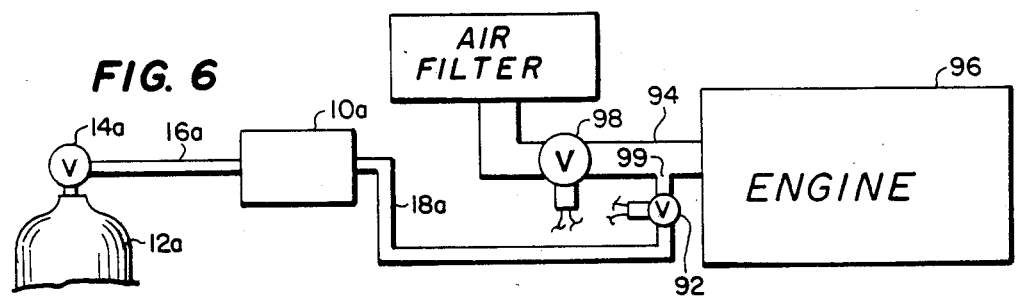
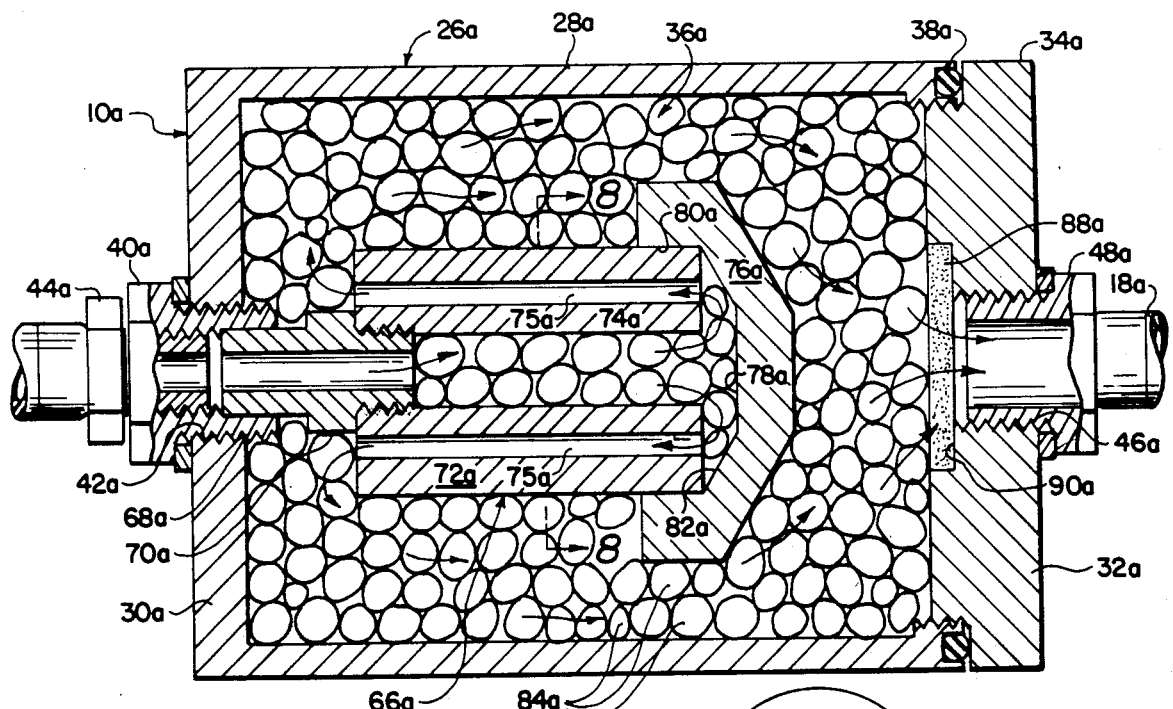
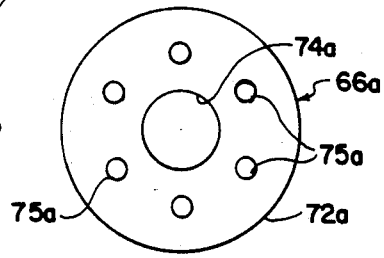

CATALYTIC HEATING SYSTEM

BACKGROUND OF THE INVENTION

1. Field of the Invention The present invention is in the field of heating air by exothermic catalytic oxidation of a small fraction of hydrogen gas mixed with the air.

2. Description of the Prior Art

There is a widespread need for apparatus capable of producing heated air for several end uses, and in most cases such need is for air heating apparatus which is self-contained, compact, and lightweight so as to be conveniently portable The most important current need for such air heating apparatus is to produce heated air to be inspired by persons through a face mask or other suitable device into the lungs, which is an efficient means for warming persons suffering from body core heat loss that may have reached the stage of hypothermia, i.e., the body core temperature may have become reduced down to 94.0° F. or lower from the normal body core temperature of 98.6° F. Such inspiration of heated air directly into the lungs is the quickest possible way to warm a person, and it is in no way harmful, as some systems for warming a person can be; in fact, breathing heated air can be beneficial.

Much of this need for heated air is to combat hypothermia in medical emergency situations, but there is also widespread need in connection with hypothermia that is either unavoidable or deliberately induced during surgery. The medical needs for heated air to combat hypothermia are the most important present needs.

The medical emergency hypothermia problems fall into two separate categories, the "accidental hypothermia" problems and the "urban hypothermia" problems. Examples of typical accidental hypothermia situations are a car crashing into a very cold river, an accidental near-drowning, a child lost overnight, a skiing accident, or a small boat accident in which the boat sinks or burns and its occupants must jump into very cold water. Examples of urban hypothermia are alcohol or other drug-induced cold, stroke victims, or the tendency which some older people have to run lower than normal body temperatures because of slower heart rates and blood circulation, and poor body conductivity.

There are several hypothermia problems involved in surgery. In general, every time someone undergoes surgery they are placed in an environment where they have a minimal amount of clothing, especially if they are having major surgery where there is no clothing involved and there are just a few surgical drapes. All surgical patients are affected by hypothermia, the degree of which is determined at least in part by the length of the surgical procedure. Hypothermia is the greatest problem for anesthesiologists. Hypothermia otherwise caused during surgery complicates the anesthetic application problems. Also, the anesthetic gases and some other anesthetic agents will produce slower blood flows and other metabolic changes which will induce hypothermia. It is recognized that eight of the thirteen commonly used anesthetics produce hypothermia. Additionally, during organ transplant and heart surgical procedures the patient is routinely cooled to a temperature far below the 94.0° F. hypothermia level, commonly to approximately 77° F., and in some instances to as low as 68° F. To indicate the extent of this problem, there are approximately 240,000 heart procedures performed each year.

The important thing in such surgical hypothermia is to be able to control the body core temperature of the patient. Regardless of whether the hypothermia is deliberately or inadvertently induced during surgery, it is important to be able to rewarm the patient quickly and safely. The problem now is that the rewarming techniques employed in recovery after surgery are slow, and some of them can cause damage. One rewarming technique is the use of heating blankets, but this is very slow. Another common technique is to use a blood warming device on the profusion pump, which in layman's terms is the heart/lung machine. However, if the heart/lung machine is depended upon to rewarm the body, the longer it is necessary to circulate the blood through the machine, the more hemolysis that is caused (hemolysis being the breaking apart of red blood cells). Thus, most currently used rewarming techniques after surgery are external to the body.

However, it has been determined that rewarming the patient internally by having the patient breathe warm air is a more effective way of heating the body from a hypothermic condition. The most current apparatus that is used in medicine for this purpose is made by Bennett-Cascade, this apparatus having an electrically powered heat source over which water is cascaded every time the patient breathes in. However, this has the problems that there is very little temperature control, and a temperature gradient of at least about 10° F. in the delivery tubing tends to cause a considerable amount of water condensation in the tubing which, if it enters the lungs, can restrict the amount of gas exchange in the lungs. Additionally, as a patient starts to awaken, he will tend to fight off the heavy humidity and extra water.

Another serious hypothermia problem is one that can accidentally occur during deep sea diving, particularly commercial diving. Divers will routinely work in the range of from about 700-1300 foot depths out of a diving bell or platform, and during these operations they are warmed by hot water suits. Under normal conditions without the hot water suits, all of the metabolic production of heat at such depths where the temperature is 39.4° F. is lost through the respiration regardless of what is done to protect the body. Even with the hot water suits the divers are losing heat, but once the hot water suits are cut off from their source of hot water, as in an emergency, suddenly the divers are in a grave situation. The diving bell or platform will normally have from seven to nine cylinders of a compressed helium/oxygen gas so that there would be enough of such artificial air mix to last approximately three days. However, the divers would freeze to death, even in survival suits, within eight hours. Thus, there is an important need for warm air breathing apparatus to cope with hypothermia in diving situations. By inspiring warm air directly into the body via the lungs, the heat losses from the severe cold and high thermal outlet conductivity of the salt water can be completely overcome.

There are a number of institutions and geographical regions where it would be highly desirable to have apparatus for providing warm breathing air that is self-contained, compact, light in weight and readily portable. Examples of these are the military for coping with a variety of military-type accidents; the Coast Guard for small vessel rescue work; ski resorts because of the frequency of ski accidents and the severe cold environment; mountain communities; and expeditions to colder climates such as Antarctica, and Nepal and Switzerland where a great deal of mountain climbing occurs. In remote locations such as these people are often days away from any help, so that they would usually die without the prompt thermal help against hypothermia that would be available with warm air breathing apparatus.

While it will be seen from the foregoing that the principal uses currently envisioned for a catalytic air heating system are for warming air or other breathing gas to combat hypothermia, there are other currently envisioned uses for a catalytic air heating system. One of these is for warming the intake air of an internal combustion engine to improve fuel vaporization in a cold climate situation. Another is the warming of an electric storage battery by enshrouding it in heated air. Another is for warming a space, such as a room or rooms of a building.

Applicant is aware of the Castel U.S. Pat. No. 4,016,878 which teaches the heating of breathing air by the exothermic oxidation of a small percentage of hydrogen gas mixed with the air. The Castel patent teaches storing the air/hydrogen mixture in a pressure cylinder and releasing it through a catalyst bed in a simple straight-through flow to a breathing mouthpiece or mask. While the Castel system does indeed heat the breathing air, it is much too slow in building up sufficient heat to reach a target temperature, and large temperature fluctuations occur between inspiration and expiration. For these reasons, the Castel apparatus has not found commercial acceptance for combating hypothermia in the many situations where air warming apparatus could be useful as indicated above.

SUMMARY OF THE INVENTION

In view of these and other problems in the art, it is a general object of the present invention to provide improved apparatus and method for heating an oxidizing gas, usually air, by the exothermic catalytic oxidation of a small percentage of hydrogen gas that is mixed with the air or other oxidizing gas.

Another object of the invention is to provide a catalytic heating system for heating air or other oxidizing gas by the exothermic oxidation of a small percentage of hydrogen therein which is capable of achieving a target temperature surprisingly rapidly; where the air or other oxidizing gas is breathing air that is to be heated, a target temperature of 104° F. being achievable with only approximately 4 to 8 breaths.

Another object of the invention is to provide a catalytic heating system of the character described which is capable of heating air or other oxidizing gas to a target temperature at which there surprisingly is no substantial temperature fluctuation, even though there may be large fluctuations in the gas flow, such as when the system is employed to provide breathing air or other breathing gas mixture.

Another object of the invention is to provide an air/hydrogen catalytic heating system that is particularly suitable for warming a person who is suffering from hypothermia or is approaching hypothermia, as for example in cases of medical emergency including accidental hypothermia and urban hypothermia, in surgical situations where the hypothermia is either deliberately or accidentally induced in the patient, or in very cold environmental situations such as that which may be encountered in a deep sea diving accident, boating accident or skiing accident, or on expeditions to regions having very cold climates, such as Anarctica, Nepal or Switzerland.

Another object of the invention is to provide a catalytic heating system of the character described which is self-contained, compact, light in weight and readily transportable, yet which has a capacity for providing heated air over an extended period of time.

Another object of the invention is to provide a catalytic heater module which is extremely durable, being able to withstand the high pressures of a deep sea diving environment, and the tortures of military use.

Another object of the invention is to provide a catalytic heating system of the character described which is suitable for a variety of other uses in addition to the heating of breathing air to combat hypothermia, including but not limited to such uses as the warming of intake air of an internal combustion engine to improve fuel vaporization in a cold climate, the warming of an electric storage battery by flowing the heated air around the battery, or the warming of an enclosed space such as a room or rooms of a building.

A further object of the invention is to provide a catalytic heater unit which embodies a catalytic preheat core chamber within the primary catalytic reaction chamber, such preheat core elevating the overall temperature of the catalyst bed which, according to a law of thermodynamics, makes the entire system more efficient and thereby increases the heat generated while nevertheless enabling the percentage of the oxidized gas, hydrogen, that is to be materially reduced.

A further object of the invention is to provide a catalytic heater unit of the character described wherein the catalytic preheat chamber is defined within heat sink structure that serves to stabilize the temperature of the more efficiently heated air, even with wide fluctuations in the flow of air through the unit such as are produced by breathing when the unit is employed to provide heated breathing air.

A still further object of the invention is to provide a catalytic heater of the character described wherein heat sink preheat core structure within the primary reaction chamber catalyst bed provides an extended flow path to increase the residency time, and hence contact time, of the preheated air within the core structure and thereby even further increases the efficiency of the system.

The present invention is an improved catalytic heater adapted primarily for heating air that is to be breathed for overcoming hypothermia, but also usable for heating other oxidizing gases, as for example a helium/oxygen mixture such as is employed in deep sea diving. The invention also resides in a new method of utilizing a preheater heat sink core within the primary reaction chamber of the catalytic heater so as to elevate the temperatures of both the preheat catalyst bed and the primary catalyst bed which greatly increases the thermodynamic efficiency to produce a higher heated gas output temperature with less fuel and to provide a stabilized temperature of the output gas despite wide fluctions in the flow through the catalytic heater.

The catalytically oxidized fuel is a small percentage of hydrogen gas in the air or other oxidizing gas to be heated, as for example approximately 0.1 percent by volume of hydrogen in air when the air is being heated for the breathing purpose, or approximately 2.5 percent hydrogen in air if the heated air is to be used as intake air for an internal combustion engine.

According to the invention, a preferably cylindrical catalyst container receives an air/hydrogen mixture from a pressurized cylinder axially through an inlet end wall thereof, and this air/hydrogen mixture is fed into a small preheat reaction chamber filled with catalyst pellets that is defined within a heat sink cylinder coaxially and generally centrally located within a larger, primary catalytic reaction chamber defined within the cylindrical catalyst container. The exothermic catalytic oxidation of the hydrogen immediately commences upon contact of the air/hydrogen mixture with the catalyst in the central preheat reaction chamber, and this heated air/hydrogen mixture is then redirected 180° by a heat sink end cap over the heat sink cylinder and passes through a plurality of regularly annularly-spaced longitudinal preheat passages that extend through the heat sink cylinder so as to further heat the heat sink cylinder substantially uniformly around its annulus.

The heated air/hydrogen mixture then flows into the primary catalytic reaction chamber and is again diverted 180° back to its initial axial flow direction and passes through the primary catalyst bed external to the heat sink cylinder, and then axially out through the outlet end wall of the cylindrical catalyst container. The primary heating of the air occurs by catalytic oxidation of the remainder of the hydrogen in the primary reaction chamber, and this provides even further heat to the preheater heat sink core which consists of the heat sink cylinder, its end cap, and also its inlet and support tube at its opposite end from the cap. The preheater heat sink core is massive and is made of a dense metal that has good heat retention and thermal inertia characteristics, such as brass.

The initial heating of the air/hydrogen mixture in the preheat reaction chamber, the heating of preheater core members by contact of this heated air therewith, and particularly by added contact of the preheated air with the heat sink cylinder as it passes through the plurality of longitudinal preheat passages through its wall, the increased thermodynamic efficiency of the catalytic reaction in the primary catalyst bed because of the fact that the air has been preheated, and then the further heating of the preheater heat sink members because of their association with the hotter air in the primary catalytic bed, all cooperate to enable the catalytic heater of the invention to heat air to a higher temperature with a considerably lower percentage of the hydrogen fuel contained in the air than was possible with the straight-through travel of the air/hydrogen mixture through the catalyst bed as taught in the Castel U.S. Pat. No. 4,016,878.

The heat sink quality of the central core preheater causes it to function in a stable manner despite wide fluctuations in the flow of the air/hydrogen mixture through the preheater, as will occur when the heated air is used for breathing purposes, so that there is no substantial fluctuation of the temperature of the heated air despite such fluctuations in the flow of the air/hydrogen mixture through the catalytic heater of the invention.

A tough plastic outer case is preferably provided over the cylindrical catalyst container with an insulative air space therebetween, to strengthen the catalytic heater against damage in adverse survival conditions and to minimize heat loss from the catalyst container.

BRIEF DESCRIPTION OF THE DRAWINGS

These and other objects of the invention will become more apparent in view of the following description and the accompanying drawings, wherein:

FIG. 1 is a perspective view illustrating the catalytic heater of the present invention embodied in a self-contained system adapted for warming a person who is suffering from hypothermia;

FIG. 2 is a side elevational view of the catalytic heater shown in FIG. 1;

FIG. 3 is an enlarged axial section taken on the line 3-3 in FIG. 2, with portions shown in elevation, showing internal details of construction of the catalytic heater shown in FIG. 1;

FIG. 4 is a fragmentary transverse section taken on the line 4—4 in FIG. 3;

FIG. 5 is a transverse section taken on the line 5—5 in FIG. 3, but reduced from the scale of FIG. 3 and in the same scale as FIG. 2;

FIG. 6 shows a second form of catalytic heater according to the invention which is coupled into a system adapted for heating the intake air of an internal combustion engine;

FIG. 7 is an axial sectional view similar to FIG. 3, with portions in elevation, showing internal details of construction of the catalytic heater shown in FIG. 6; and FIG. 8 is a fragmentary transverse section taken on the line 8—8 in FIG. 7.

DETAILED DESCRIPTION

Referring to the drawings, and at first particularly to FIG. 1 thereof, one form of catalytic heater embodying the present invention is generally designated 10, and it is illustrated coupled into a self-contained system adapted for warming a person who is suffering from body core heat loss that may have reached the stage of hypothermia, i.e., the body core temperature may have become reduced from the normal 98.6° F. down to 94.0° F. or lower. Such hypothermic condition may have been caused by any of the situations discussed hereinabove, as for example by a medical emergency involving either accidental hypothermia or urban hypothermia; deliberately during surgery, such as during heart surgery or organ transplant surgery, or unavoidably and undesirably during surgery because of minimal clothing or anesthetics; or in a very cold environment, such as that which may be encountered in a deep sea diving accident or on an expedition to a region having a very cold climate.

In the system illustrated in FIG. 1, a mixture of air and hydrogen gas is provided under very high pressure, which may be up to approximately 2200 psig, in a pressurized cylinder or tank 12. With the use of the catalytic heater 10 of the present invention, approximately 1.0 percent by volume of hydrogen ($H_2$) is sufficient to provide a target heated air temperature of a stable 104.0° F. It is to be understood, however, that hydrogen/air mixtures up to approximately 3.0 percent by volume of hydrogen are safe against ignition or explosion.

The air/hydrogen mixture is fed from the cylinder 12 through a pressure regulator 14 and an input hose 16 to the catalytic heater 10 where it is heated by exothermic oxidation reaction between the hydrogen and a very small fraction of the oxygen in the air, the heated air then passing through an output hose 18 to a demand valve 20, and thence on demand through a rigid conduit 22 to a breathing mask 24, from which the warmed air may be inspired by a person suffering from hypothermia or a lowered body core temperature approaching hypothermia. The pressure regulator 14 is a first stage-type regulator, and preferably provides an output delivery pressure of approximately 50 psig above ambient pressure for the particular environment. Thus, for example, if the apparatus is being used to combat hypothermia in a diving accident wherein the marine depth is approximately 1,000 feet and the ambient marine pressure is approximately 300 psig, then the pressure regulator 14 will deliver the air/hydrogen mixture at a pressure of approximately 350 psig. If, on the other hand, the apparatus is being used in a medical emergency on land proximate sea level, then the pressure regulator will deliver the air/hydrogen mixture at a pressure of approximately 50 psig.

only a 1.0 percent hydrogen mixture with air is employed, then since the product of the exothermic reaction is water ($H_2O$), only 0.5 percent of the oxygen contained in the heated breathing air will be used for the reaction, which is such a minimal fraction of the oxygen in the air that it has no adverse effect upon breathing. The water produced by the reaction provides approximately 18 percent relative humidity to the breathing air (the highly compressed air in the pressurized cylinder 12 being dehydrated before it is introduced into the cylinder 12). At normal body temperature, which is 98.6° F., there is approximately 47 percent relative humidity inside of the bronchial tubes and the lungs, so it may be desirable to increase the approximately 18 percent relative humidity of the breathing gas provided by the present system up to approximately the normal 47 percent bronchial and lung humidity, or even higher, by connecting a conventional nebulizer (not shown) into the system, preferably by connecting it with the tube 22. Such prevention of further dehydration of a patient is particularly important in cases of accidental hypothermia, and a patient can absorb a small amount of moisture without having the adverse effect of blocking the ability of the lungs to exchange gases, and this being of particular importance if the patient is comatose because in that condition there is not an extra residual of lung volume.

The demand valve 20 and tube 22 are preferably made primarily of a plastic material having good thermal insulation properties to minimize heat loss in these regions. The demand valve 20 may be any commercially available demand valve. The demand valve 20 that is illustrated in FIG. 1 is an Elder demand valve, which is an oxygen resuscitating-type of demand valve that is particularly suitable for the present system because it has the dual functions of working both as a manually actuated ventilator-resuscitator-type valve where the patient may be in a coma, or it can work like a scuba regulator where it delivers the heated air upon breathing demand, and does not force the heated air on the person.

Referring now to FIGS. 2-5, the catalytic heater 10, which is a form of the invention particularly suitable for the breathing use of the invention to counter hypothermia, has a cylindrical catalyst container generally designated 26 that is preferably made of metal, and is preferably either aluminum or stainless steel. Aluminum will be the usual choice because then the overall device will be much lighter in weight than if stainless steel is used. However, there will be slightly more heat loss with the use of aluminum because of its greater thermal conductivity than stainless steel. Nevertheless, the overall construction of the catalytic heater 10 for the breathing purpose includes an external cannister and associated insulating air layer which minimize thermal losses as described below despite the use of aluminum for the cylindrical catalyst container 26.

The catalyst container 26 includes a cylindrical outer wall 28, a generally disk-shaped input end wall 30 which is preferably integral with the cylindrical wall 28 as shown in FIG. 3, and an output end wall 32 which is likewise generally disk-shaped, but is formed as part of a cap for the output end of the cylindrical wall 28, having a peripheral axial flange 34 which overlies the cylindrical wall 28. The primary catalytic reaction chamber is generally designated 36, and is defined within the cylindrical wall 28 and the respective input and output end walls 30 and 32. The reaction chamber 36 is peripherally sealed at its output end by means of an O-ring seal 38 located in an axially-opening seal ring groove opening through the flat annular output end edge of cylindrical wall 28, the output end wall 32 being clamped against the seal ring by the external cannister described below.

A tubular input fitting or adapter 40 in the form of a ferrule having an external nut portion is threadedly engaged in an axially-centered threaded inlet passage 42 extending through the input end wall 30. An input hose ferrule 44 to which the input hose 16 is coupled is in turn threadedly engaged in the inlet fitting or adapter 40. A threaded outlet passage 46 extends axially through the center of the output end wall 32, and an output hose ferrule 48 to which the output hose 18 is connected is threadedly engaged in outlet passage 46.

The external cannister is generally designated 50, and it includes a cylindrical barrel 52 coaxially arranged about the periphery of cylindrical wall 28 and radially located in outwardly-spaced relationship from the outer cylindrical surface of wall 28 by means of the peripheral annular flange 34 on end wall 32 and a pair of axially-spaced external annular ribs 54 and 56 on cylindrical wall 28. A pair of end caps 58 are threadedly engaged over the respective ends of the barrel 52, the end caps 58 having flat annular end portions 59 which overlie the input and output end walls 30 and 32, respectively. An O-ring seal 60 is disposed in an annular seal ring groove opening through the outer surface of each end wall 30 and 32, the seal rings 60 being coaxial with the respective end walls 30 and 32 and being tightly engaged by the flat annular end portions 59 of caps 58 so as to seal in the air within the annular thermal insulation air space 57 between cylindrical wall 28 and cylindrical barrel 52. Also, as seen in FIG. 3, there will be some thermal insulation air sealed in the end spaces between the end walls 30 and 32 and the flat annular end portions 59 of the respective caps 58.

A thin, sheet-like temperature scale 62 is bonded to the outer surface of the cylindrical wall 28 of catalyst container 26 to indicate the heated temperature of the container 26; while a similar temperature scale 64 is bonded to the outer surface of the cylindrical barrel 52 to indicate substantially ambient temperature. These temperature scales 62 and 64 are of the type whereon colored dots 65 sequentially become prominent as the temperature raises or lowers.

The barrel 52 and end caps 58 of cannister 50 are preferably made of a very strong polycarbonate material, and at least the barrel 52 is made transparent so that the inner temperature scale 62 is visible therethrough.

O-ring seals 38 and 60 are made of an elastomeric material that will provide a positive seal over a long operational life, despite the elevated temperatures produced during operation of the catalytic heater 10. The primary purpose of the seals 38 and 60 is to exclude water from the reaction chamber 36 and the catalyst therein. Examples of suitable materials for the seals 38 and 60 are buna-N, and "Viton," which is an engineering grade elastomer that is available from Parker Seals.

The preheater heat sink of the present invention is generally designated 66 and is axially located as a central core within the reaction chamber 36. The preheater heat sink 66 actually comprises three physically and thermally connected elements, two of which are the principal thermal elements and which are not only coaxially located about the central axis of the catalyst container 26 but are also generally longitudinally centrally located within the reaction chamber 36. The third element of the preheater heat sink 66 that is not generally longitudinally centered in reaction chamber 36 is an inlet and support tube 68 which has an unthreaded end portion 69 that is press-fitted into a complementary unthreaded bore portion of the inlet fitting or adapter 40. The preheater heat sink inlet and support tube 68 has an external locating collar 70 thereon.

The primary, most important of the three elements of preheater heat sink 66 is a thick-walled preheater heat sink cylinder 72 that is coaxially arranged within the reaction chamber 36. The cylinder 72 is threadedly mounted on the inner end portion of inlet and support tube 68, being generally centrally located within reaction chamber 36 by abutment against the locating collar 70 on inlet and support tube 68. The preheater heat sink cylinder 72 defines within its annular bore a preheat reaction chamber 74. A plurality of preheat passages 75 extend longitudinally through the wall of cylinder 2, opening at both ends of cylinder 72. The longitudinal passages 75 are regularly spaced around the annulus of cylinder 72, and are preferably six in number as seen in FIG. 4.

The other principal element of preheater heat sink 66 is a preheater heat sink cap 76 which is press-fitted over the end portion of cylinder 72 that is opposite the end thereof that is mounted on inlet and support tube 68. The cap 76 is a generally disk-shaped member coaxially arranged within the reaction chamber 36, and has a cupped recess 78 therein that is defined by a cylindrical entrance 80 which ends at a tapered annular frusto-conical surface 82 which leads to a flat bottom surface. The cylindrical entrance 80 of heat sink cap 76 is the portion of cap 76 that is press-fitted over the output end of cylinder 72, the end of cylinder 72 bottoming against the outer edge of frusto-conical surface 82, whereby the bottom of cupped recess 78 is axially spaced from the end of heat sink cylinder 72 and an annular clearance is defined between the end of cylinder 72 and the tapered frusto-conical surface 82 and bottom of cupped recess 78 in cap 76.

The entire reaction chamber 36, including the preheat reaction chamber 74 within heat sink cylinder 72, is filled with catalyst pellets 84. The pellets 84 are preferably substantially spherical so as to obtain the maximum contact surface area for the volume of the primary reaction chamber 36 and preheat reaction chamber 74. The presently preferred catalyst pellets 84 are platinum-coated sintered alumina pellets, with the platinum constituting approximately 1.0 percent by weight of the pellets 84. Such platinum-coated alumina spheres having diameters of approximately 4 mm have proven satisfactory in prototype catalytic heaters 10 according to the invention. Catalyst carriers other than alumina which may be used include magnesia, silica gel, diatomaceous earth, charcoal, or even metal pellets. While platinum is the preferred catalyst, other suitable catalysts include platinum oxide, and metals or metal oxides of palladium, vanadium, chromium, copper, manganese, cobalt and nickel.

The flow path of the air/hydrogen mixture through the catalytic heater 10 is indicated by arrows in FIG. 3. The air/hydrogen mixture enters heater 10 from input hose 16 through its ferrule 44 and inlet fitting or adapter 40, passing axially through the bore of preheater heat sink inlet and support tube 68 into the preheat reaction chamber 74 within cylinder 72. It is to be noted that the bore of inlet and support tube 68, and also the annular space between the bottom of cupped recess 78 and the proximate end of cylinder 72, are smaller than the diameters of the catalyst pellets 84 so as to confine the preheat pellets 84 within the preheat reaction chamber 74. The air/hydrogen mixture instantaneously commences to exothermically oxidize when it passes over the catalyst pellets 84 within preheat reaction chamber 74, and the heat thus generated raises the temperature of the gas flowing within cylinder 72 and against heat sink cap 76 so as to directly raise the temperatures of the cylinder 72 and cap 76.

The preheated air/hydrogen mixture is then channeled through the cupped recess 78 of cap 76 into the proximate ends of the longitudinal preheat passages 75 so that the preheated gas reverses its direction 180° and flows through the passages 75 the length of cylinder 72 back in the inlet direction. Because the gas flowing through longitudinal passages 75 has been preheated within preheat chamber 74, and because of the regular spacing of the passages 75 annularly about the cylinder 72, the mass of cylinder 72 is further heated substantially uniformly around its annulus.

The inside of input end wall 30 has an annular frusto-conical recess 86 therein to enable more of the catalyst pellets to be concentrated proximate the exit ends of the longitudinal preheat passages 75, and to provide a path of substantial axial extent for the preheated gas to be redirected radially-outwardly and then axially in the outlet direction through the main body of catalyst in the reaction chamber 36. The primary heating of the gas occurs in the main part of reaction chamber 36 externally of the preheater heat sink cylinder 72, and contact of the continuously heating gas with the external surfaces of inlet and support tube 68, cylinder 72 and cap 76 further heat up the entire preheater heat sink 66. Such further heating greatly increases the core temperature within the preheat reaction chamber 74, so that the gas will be more efficiently preheated and hence more efficiently oxidized both in the preheat reaction chamber 74 and in the main reaction chamber 36.

The preheat system of the present invention utilizes one of the basic laws of thermodynamics, namely, that the higher the temperature of the system, the more efficient the system becomes. By preheating the gas in the preheat reaction chamber 74, the higher temperature state of the gas as it passes through the main reaction chamber 36 causes the catalytic oxidation of the hydrogen to be more efficient in the main reaction chamber 36 and hence to heat up the air to a higher temperature before it passes out of the catalytic heater 10. Additionally, some of this higher temperature heat from the main reaction chamber 36 is conducted through the walls of preheater heat sink inlet and support tube 68, preheater heat sink cylinder 72 and preheater heat sink cap 76, to add further heat to the incoming air/hydrogen mixture as it flows through the inlet tube 68, through the preheat reaction chamber 74, against the inner wall of cap 76, and through the longitudinal passages 75, thereby further increasing the temperature in the preheat reaction chamber 74 and, according to this same law of thermodynamics, making the preheat reaction more efficient, which then synergistically makes the overall oxidation reaction within the catalytic heater 10 have even further efficiency. Such cooperation between the preheater heat sink core 66 and its reaction chamber 74 with the primary reaction chamber 36 is based to a large extent upon the generally central location of the preheater heat sink core 66 within the primary reaction chamber 36, and the doubling back of the preheated gas through the longitudinal passages 75 in cylinder 72 so as to achieve a greatly increased thermodynamically useful length of travel of the gas within the catalytic heater 10 as compared with the straight-through travel of the gas mixture through the catalyst bed as taught in the previously-discussed Castel et al U.S. Pat. No. 4,016,878.

All three portions 68, 72 and 76 of the preheater heat sink core 66 are made of a metal having the largest possible amount of heat retention mass and thermal inertia while at the same time not having a high thermal conductivity. The presently preferred metal is brass, which may be yellow brass. Brass has a very dense mass and correspondingly high heat retention capability and thermal inertia. Aluminum has been tested, but found to have too high a degree of thermal conductivity, so that with aluminum fluctuations of as much as 7° F. have been measured between input and output breaths. In contrast, essentially no temperature fluctuation at all is observable with the heat sink 66 made of brass.

The results of the preheater heat sink core system of the present invention are surprising both in the rapidity with which the target temperature is achieved and the stability of the target temperature once it has been achieved. Thus, with the present invention, utilizing a hydrogen concentration of no more than approximately 1 percent by volume, a target temperature of 104° F. is achieved with only approximately 4–8 breaths, and that target temperature is without substantial fluctuation. In contrast, with the prior art system as disclosed in the previously discussed Castel et al U.S. Pat. No. 4,016,878, utilizing a hydrogen concentration of approximately 3 percent by volume, it required approximately 20–30 breaths to achieve a target temperature of 104° F., temperature fluctuations as high as 11 degrees F. were observable between inspiration and expiration.

Calibration of the amount of catalytic material in the reaction chamber 36 and the concentration of hydrogen in the air/hydrogen mixture enables the catalytic oxidation reaction to be restricted so as to produce a controlled amount of heat and a controlled temperature of the resulting heated air.

The foregoing surprising new results achieved with the present invention when used for warming breathing air as generally arranged in FIG. 1 were achieved with a prototype catalytic heater 10 having the following approximate dimensions which are given by way of example only and not of limitation: the reaction chamber 36 within catalyst container 26 was approximately dimensionally "square" with a diameter of one and three-quarters inches and a length of one and three-quarters inches; the preheater heat sink cylinder 72 was one inch long by three-quarters inch OD and 0.477 inch ID and with each of its longitudinal preheat passages 75 having a diameter of 0.093 inch; the preheater heat sink inlet and support tube 68 was one inch long with an OD of five-sixteenths inch and an ID of one-eighth inch; and the preheater heat sink cap 76 was a disk one and one-eighth inch in diameter with a thickness of seven-thirty-seconds inch, with the cylindrical entrance portion 80 of its cupped recess 78 being one-eighth inch deep and its tapered annular surface 82 being inclined at 30° from the flat bottom surface and having a depth of one-sixteenth inch. The three portions 68, 72 and 76 of preheater heat sink core 66 were all made of yellow brass. The primary reaction chamber 36 and preheat reaction chamber 74 were filled with 24.5 grams of the 1 percent platinum by weight coated sintered alumina pellet spheres 84 of 4 mm diameter. The barrel 52 and end caps 58 of external cannister 50 were made of one-eighth inch thick clear polycarbonate material, and the thermal insulation air space 57 between the cylindrical wall 28 of the catalyst container 26 and the cannister barrel 52 was one-eighth inch in radial dimension.

The heated breathing air passes out of the main reaction chamber 36 of the catalyst container 26 through a porous sintered ceramic filter 88 that is seated in a flat annular recess 90 in output end wall 32, the heated breathing air passing out through the output hose ferrule 48 and its output hose 18.

Although the present invention will normally be employed for the heating of air supplied in an air/hydrogen mixture, it is to be understood that the invention is equally applicable to the heating of other oxidizing gases. An example of such other oxidizing gas is a helium/oxygen mixture such as is used in deep sea diving, in which case a small percentage by volume of hydrogen will be added to the mixture in a similar porportion as described above in connection with the air/hydrogen mixture.

Compactness and lightness in weight are important advantages of the present invention over other air warming systems. With the cylindrical catalyst container 26 made of 6061T6 aluminum, and filled with 24.5 grams of catalyst, the total weight of the catalytic heater 10 including the external cannister 50 is only approximately 400 grams. Portable, self-contained apparatus according to FIG. 1 particularly suitable for survival and expedition uses weighs only approximately 9 pounds.

With the polycarbonate external cannister 50 the catalytic heater 10 of the invention is extremely tough and durable, which are attributes of special importance for some uses such as under the high pressures encountered in deep sea diving and when used by the military which needs apparatus that can withstand considerable torture. The strength and durability are also important for emergency and survival uses where operations are often moving very rapidly and accidental mishandling of the equipment can occur, yet where it is essential that the equipment always reliably perform.

FIGS. 6–8 illustrate a second form of catalytic heater according to the invention which is generally designated 10a, and it is illustrated coupled into a system adapted for heating the intake air of an internal combustion engine to assist vaporization of the fuel under very cold starting conditions. When the ambient temperature gets down below about 10°–20° F., internal combustion engine fuels, and particularly diesel fuel, will not vaporize as well as at higher temperatures, and good vaporization thereof is essential for the internal combustion engine to work.

In the system illustrated in FIG. 6, the high pressure mixture of air and hydrogen is provided in pressurized cylinder or tank 12a having output pressure regulator 14a which regulates the output pressure to a suitable value for the purpose, which may again be approximately 50 psig. The air/hydrogen mixture is preferably a "hotter" one than for the breathing purpose, and a presently preferred mixture includes approximately 2.5 percent by volume of hydrogen, which enables the heated air to be heated up to temperatures on the order of about 200° F.

The air/hydrogen mixture is fed from pressure regulator 14a through an input conduit 16a to the catalytic heater 10a, and the heated output air from the heater 10a is delivered through an output conduit 18a and a valve 92 to the air intake conduit 94 of internal combustion engine 96. Preferably, the valve 92 is temperature controlled in cooperation with a choke valve 98 that is upstream of the port 99 through which the heated air is delivered from valve 92. Preferably both of the valves 92 and 98 are electrically actuated in the same manner as current state-of-the-art choke valves. According to how cold the ambient temperature is, the choke valve 98 will either partially or fully close, and the hot air input valve 92 will partially or fully open to supply the heated air to the engine 96. Then, as the engine 96 warms up, the choke valve 98 will open up and the hot air input valve 92 will close down as required.

The catalytic heater 10a that is used for this engine intake air heating purpose is preferably considerably larger than the catalytic heater 10 utilized for the breathing purpose, because of the greater requirement for the flow of heated air. Also, weight is not a problem in the engine usage. Further, the insulating and strengthening characteristics imparted to the breathing catalytic heater 10 by the external cannister 50 are not required for the vehicle intake usage. Thus, a prototype catalytic heater 10a for the engine intake purpose worked satisfactorily with a cylindrical catalyst container 26a that held approximately 125 grams of the same type of catalyst pellets as described above that are employed in the catalytic heater 10.

The cylindrical catalyst container 26a of catalytic heater 10a includes a cylindrical outer wall 28a having an integral, disk-shaped input end wall 30a and an output end wall 32a that is also generally disk-shaped, but is formed as a cap for the output end of the cylindrical wall 18a, being threadedly engaged within the output end of the cylindrical wall 28a and having a peripheral radial flange 34a which seats against an O-ring seal 38a set in a seal ring groove that opens out through the annular output end surface of cylindrical wall 28a. The main reaction chamber is designated 36a and is defined within the walls 28a, 30a and 32a.

A tubular input fitting or adapter 40a is threadedly engaged in axially-centered threaded inlet passage 42a through input end wall 30a, and an input conduit ferrule 44a to which input conduit 16a is coupled is in turn threadedly engaged in the inlet fitting or adapter 40a. A threaded outlet passage 46a extends axially through the center of output end wall 32a, and an output conduit ferrule 48a to which output conduit 18a is connected is threadedly engaged in this outlet passage 46a.

The preheater heat sink core 66a that is axially centered within the cylindrical catalyst container 26a is of substantially the same construction as the preheater heat sink core 66 in the form 10 of the invention as shown in FIGS. 3, 4 and 5. Thus, the preheater heat sink 66a includes heat sink inlet and support tube 68a which has an unthreaded end portion that is press-fitted into a complementary unthreaded bore portion of the inlet fitting or adapter 40a, the preheater heat sink inlet and support 68a having an external locating collar 70a thereon. Preheater heat sink cylinder 72a is threadedly mounted on the inner end portion of inlet and support tube 68a, being axially located by abutment against the collar 70a and being coaxially centered within the reaction chamber 36a. The cylinder 72a defines preheat reaction chamber 74a within its annular bore, and a plurality of preheat passages 75a, preferably six in number, are regularly spaced around the cylinder 72a, extending longitudinally through the wall of cylinder 72a so as to open at both ends of cylinder 72a. The preheater heat sink core 66a also includes preheater heat sink cap 76a which is press-fitted over the outlet end portion of cylinder 72a, the cap 76a being coaxially arranged within reaction chamber 36a and having cupped recess 78a therein that is defined by cylindrical entrance 80a and frusto-conical surface 82a which leads to a flat bottom surface. The cylindrical entrance 80a of cap 76a is press-fitted over the end of cylinder 72a that is opposite the end thereof that is mounted on inlet and support tube 68a, with the end of cylinder 72a bottoming against the outer edge of frusto-conical surface 82a, leaving the bottom of cupped recess 78a axially spaced from the end of cylinder 72a to provide clearance for the passage of the air/hydrogen mixture from the preheat reaction chamber 74a radially outwardly and thence into the longitudinal preheat passages 75a.

Both the preheat reaction chamber 74a and the main reaction chamber 36a are completely filled with catalyst pellets 84a which may be the same catalyst pellets as the pellets 84 described in detail hereinabove in connection with the catalytic heater 10. The heated air from the exothermic catalytic oxidation of hydrogen flows through the same path as described in detail hereinabove in connection with catalytic heater 10, and leaves the main reaction chamber 36a by passing through a porous sintered ceramic filter disk 88a that is seated in a flat annular recess 90a in output end wall 32a, the heated air passing out through the output conduit ferrule 48a and output conduit 18a for use as needed in the engine 96 according to the setting of valve 92.

The mode of operation and surprising new results of the preheater heat sink core 66a in catalytic heater 10a is identical to that described hereinabove for the preheater heat sink core 60 of the catalytic heater 10.

Although the catalytic heaters 10 and 10a have been described hereinabove for the respective end uses of heating breathing air or other gas and for heating internal combustion engine intake air, it is to be understood that the invention may also be used for other end uses where it is desired to heat air or some other oxidizing gas. For example, the invention may be utilized for space heating such as for the heating of air that is pumped into any space that is to be heated, such as the rooms of a building. As another example, the invention may be used to heat air which is flowed over an electrical storage battery to heat the battery so as to improve its performance where it had become too cold for optimum or perhaps even useful performance due to a very cold ambient condition. Other such uses will suggest themselves to one skilled in the art.

While the present invention has been shown and described herein in what are conceived to the most practical and preferred embodiments, it is recognized that departures may be made therefrom within the scope of the invention, which is therefore not to be limited to the details disclosed herein, but is to be accorded the full scope of the appended claims.

I claim:

1. A catalytic heater for heating an oxidizing gas from a source that contains a small percentage of a catalytically oxidizable gas, which comprises:

a catalyst container containing an oxidation catalyst and having spaced inlet and outlet openings at opposite ends of a flow path for said gas through said container and defining a primary catalytic reaction chamber;

a preheat catalytic reaction chamber also containing an oxidation catalyst within said primary chamber, said preheat chamber being disposed at the beginning of said flow path and having an inlet connected to said container inlet opening and an outlet that opens into the inlet end of a heat sink within said primary chamber;

said heat sink having said inlet end and an outlet end, containing no catalyst and disposed in said flow path at the outlet end of said preheat chamber, having said outlet end of said heat sink opening into said primary chamber and disposed adjacent to said preheat chamber to receive evolved heat therefrom;

said source of an oxidizing breathing gas containing a small percentage of hydrogen, said source being operatively connected to said inlet opening of said container; and breathing apparatus operatively connected to said outlet opening of said container;

whereby said gas supplied to said heater will first be catalytically preheated as it passes through said preheat chamber, further non-catalytically heated from said preheater as it passes through said heat sink and thereafter still further heated with increased thermodynamic efficiency because of said previous heating as it passes through said primary chamber.

2. A catalytic heater as defined in claim 1, wherein said breathing gas is air.

3. A catalytic heater as defined in claim 1, wherein said breathing gas comprises a mixture of helium and oxygen.

* * * * *